United States Patent [19]
Tepper et al.

[11] Patent Number: 5,743,844
[45] Date of Patent: Apr. 28, 1998

[54] HIGH EFFICIENCY PULSED ELECTROMAGNETIC FIELD (PEMF) STIMULATION THERAPY METHOD AND SYSTEM

[75] Inventors: John C. Tepper, Carrollton; Peter Kuo, Richardson; Thomas M. Emge, Sachse, all of Tex.; William L. Winstrom, Andover, N.J.

[73] Assignee: AMEI Technologies, Inc., Wilmington, Del.

[21] Appl. No.: 742,512

[22] Filed: Nov. 1, 1996

[51] Int. Cl.$^6$ .................. A61N 2/00; A61N 2/02
[52] U.S. Cl. ................. 600/14; 600/13; 600/15; 600/9; 607/2
[58] Field of Search ............... 607/2, 2 A, 2 B, 607/51; 600/13, 14, 15

[56] References Cited

U.S. PATENT DOCUMENTS

| | | | |
|---|---|---|---|
| 4,548,208 | 10/1985 | Niemi | 600/14 |
| 5,058,582 | 10/1991 | Thaler | 607/2 |
| 5,066,272 | 11/1991 | Eaton et al. | 600/14 |
| 5,181,902 | 1/1993 | Erickson et al. | 600/13 |
| 5,195,941 | 3/1993 | Erickson et al. | 600/14 |
| 5,314,401 | 5/1994 | Tepper | 600/14 |
| 5,338,286 | 8/1994 | Abbott et al. | 600/14 |
| 5,518,496 | 5/1996 | McLeod et al. | 600/14 |

*Primary Examiner*—William E. Kamm
*Assistant Examiner*—Carl H. Layno
*Attorney, Agent, or Firm*—Baker & Botts, L.L.P.

[57] ABSTRACT

A PEMF stimulation therapy system uses a PEMF transducer coil for generating PEMF stimulation signals and includes a single-winding transducer coil. A drive circuit recovers flyback energy from the single-winding transducer coil and dumps the voltage to a voltage supply equal to a predetermined high voltage that differs from supply voltage. This permits sequencing the current through the PEMF transducer coil in a positive direction and then negative direction. The result is a PEMF stimulation therapy system that may use a commercially available, low-cost battery for power and that is significantly lighter and more portable than known PEMF stimulation therapy systems.

13 Claims, 4 Drawing Sheets

| PARAMETER | SYMBOL | REQUIREMENT | UNITS |
|---|---|---|---|
| BURST INTERVAL | $T_{bi}$ | 670 ± 3 | ms |
| FIRST PULSE WIDTH (+) | $t_{pwf}(+)$ | 33 ± 3 | $\mu s$ |
| PULSE WIDTH (+) | $t_{pw}(+)$ | 65 ± 3 | $\mu s$ |
| PULSE WIDTH (−) | $t_{pw}(-)$ | 195 ± 10 | $\mu s$ |
| PULSES PER BURST | $N_p$ | 99 | − |

HIGH EFFICIENCY PULSED ELECTROMAGNETIC FIELD (PEMF) STIMULATION THERAPY METHOD AND SYSTEM

TECHNICAL FIELD OF THE INVENTION

This invention relates generally to pulsed electromagnetic field (PEMF) therapy that promotes healing of skeletal bones and body tissues, and more particularly relates to a PEMF system that uses a PEMF transducer having a high-efficiency single-winding coil for providing PEMF therapeutic stimulation to a target area of the skeletal system, and a method of fabricating the PEMF system.

BACKGROUND OF THE INVENTION

Pulsed electromagnetic fields (PEMF) are low-energy, time-varying magnetic fields that are useful for treating therapeutically resistant problems of the musculoskeletal system. Those problems include spinal fusion, un-united fractures, failed arthrodeses, osteonecrosis, and chronic refractory tendinitis, decubitus ulcers and ligament, tendon injuries, osteoporosis, and Charcot foot. For PEMF therapy, an electromagnetic transducer coil is placed in the vicinity of the musculoskeletal injury such that pulsing the PEMF transducer produces an applied or driving field that penetrates to the underlying bone.

Present day PEMF transducers use too much energy, requiring that products that use them have a rechargeable battery pack, either a nickel cadmium or nickel metal hydride battery. Rechargeable battery packs are expensive, heavy, and must be carried by the patient. Existing PEMF transducers must also be recharged nightly, which increases the cost of operating PEMF devices and makes them quite inconvenient.

The weight of PEMF bone growth stimulators is directly proportional to the size of the batteries required to generate a therapeutic signal. The comfort of these devices is inversely proportional to the weight. Any means to reduce the battery size and weight will help to directly reduce the weight and cost of such a device, and improve the user's comfort. Therefore, there is a need for a way to make PEMF systems lighter and more energy efficient.

SUMMARY OF THE INVENTION

The present invention provides a PEMF stimulation therapy system having a single-winding PEMF transducer that consumes less energy, is lighter and is easier to use than known PEMF systems.

In one aspect the present invention provides a PEMF stimulation therapy system that includes a single-winding transducer coil for generating a PEMF stimulation therapy signal that promotes healing of musculoskeletal body tissue. The PEMF stimulation therapy system includes a drive circuit for recovering flyback energy from the single-winding transducer coil and dumping a voltage equal to a predetermined amount, such as four times the battery voltage, for permitting sequencing of the current through the transducer coil in both a positive direction and negative direction. This permits the peak current to be lowered by one-half, resulting in a four-times reduction in $I^2R$ losses. Because of the lowered $I^2R$ losses, the present invention requires less power.

According to another aspect, the present invention provides a PEMF stimulation therapy system having a single-winding transducer coil and drive circuitry for driving the single-winding transducer while recovering the energy stored in the coil's magnetic field. This eliminates the need for a secondary coil winding, thereby reducing the transducer weight and power consumption. The flyback energy of the transducer coil is dumped in the preferred embodiment to a separate supply voltage that equals four times the normal battery voltage. This voltage is then available to supply current during the next pulse of the device. By having a voltage equal to four times the battery voltage available, current through the transducer coil can be sequenced, in much the same way as is done with a full-bridge or half-bridge circuit, to go in both directions. Therefore, for a given magnetic field strength, the peak current can be cut in half, resulting in a factor of four reduction in $I^2R$ losses. This drive circuit, instead of using a separate four times supply voltage boost circuit, uses its own flyback pulse to derive the voltage.

This energy recovery without a secondary coil is more efficient, because there are no coupling losses that inevitably arise with a secondary coil (i.e., there is no leakage inductance). In addition, the single-winding transducer coil possesses the technical advantage of being simpler and less expensive to manufacture.

Another technical advantage of the present invention is that because it includes fewer windings to generate the desired magnetic field, there are fewer electrical connections. This makes the resulting PEMF device more reliable while also being more energy efficient.

Another technical advantage of the present invention is that the PEMF transducer of the present invention may generate more than one type of PEMF signal. All of the generated signals from the PEMF transducer device are high efficiency, but the highest frequency signals are more efficient. The present invention may, by using a higher frequency input, generate a much more energy efficient signal. For example, one signal may be as much as 16 times more energy efficient while providing the same or similar quality of PEMF therapy as the prior known signals.

Another technical advantage of the present invention relates to the simple economics of producing a system that requires only a single PEMF transducer coil. The present invention avoids the manufacturing costs of a double winding and the associated weight of a two-winding circuit. Moreover, using a single winding permits the driver circuit of the present invention to energize only the single winding and then recover from the single winding part of the energy necessary to generate the next PEMF stimulation therapy signal.

Another technical advantage of the present invention is that it provides a "bi-phasic" process in which current passes through the single winding in two directions. A first direction signal generates the PEMF field. Then, with the signal in a second direction, the present invention recovers the PEMF energy generated by the first direction signal. With the bi-phasic technique, current goes from a positive level through zero to a negative level. The result is that the amount of positive voltage, resulting current and, therefore, the energy loss decreases substantially. For the same swing in current, by virtue of going from a negative value to a positive value, a four-fold reduction in current loss occurs. Accordingly, wire heat losses are minimized, and the wire gauge may be smaller. This further helps to make the resulting PEMF transducer lighter and economical to manufacture. The ultimate result is, therefore, a more comfortable, less expensive PEMF stimulation therapy system.

Another technical advantage of the present invention is that because the PEMF transducer is more energy efficient, it is possible to use a smaller, lighter, non-rechargeable battery. The present invention may use, for example, a commercially-available nine-volt lithium or alkaline non-rechargeable battery. These batteries are manufactured in high volumes, with great reliability and may be disposed of after they lose their charge. Consequently, the present invention eliminates the need for a battery charger and avoids the possibility of electrical shock from operating the charger, as well as the cost of the charging device, itself.

BRIEF DESCRIPTION OF THE DRAWINGS

For a more complete understanding of the present invention and the advantages thereof, reference is now made to the following description which is to be taken in conjunction with the accompanying drawings in which like reference numerals indicate like features and wherein.

DETAILED DESCRIPTION OF ILLUSTRATIVE EMBODIMENTS

Preferred embodiments of the present invention are illustrated in the FIGUREs wherein like numerals refer to like and corresponding parts of the various drawings. This detailed description of illustrative embodiments of the PEMF stimulation therapy system is organized as follows:

1. PEMF stimulation therapy system and transducer;
2. PEMF transducer design and fabrication;
3. Control and drive electronics; and
4. Conclusion.

1. PEMF Therapeutic Stimulation System and Transducer

The exemplary embodiments of the PEMF transducer system are configured to provide PEMF stimulation therapy for the shoulder, the hands, the hip, or essentially any other bone structure of the body to assist in healing objectives such as fusion repair.

Figure 1:
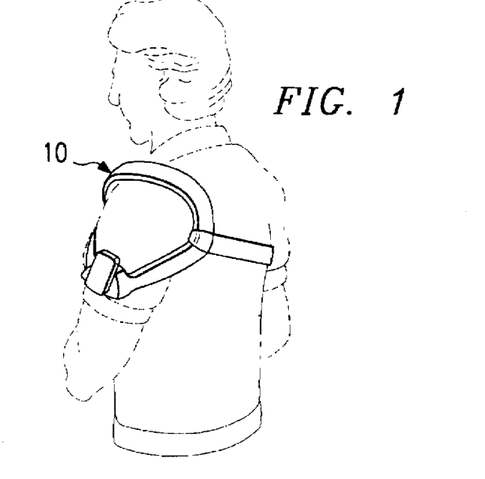
FIGS. 1 through 3 illustrate several different examples of a PEMF stimulation therapy system formed according to teachings of the present invention.
Figure 2:
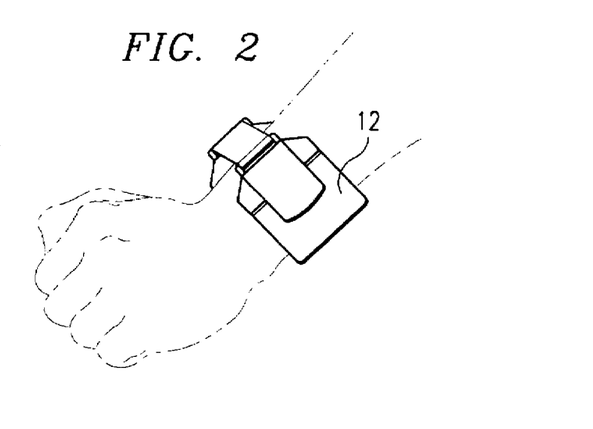
Figure 3:
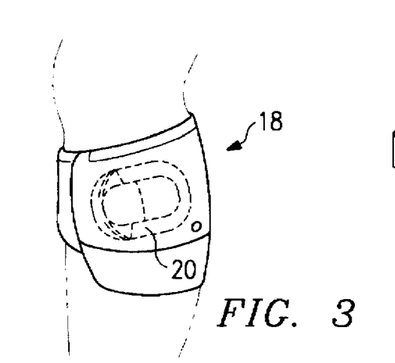

FIGS. 1 through 3 illustrate several different examples of a PEMF stimulation therapy system formed according to teachings of the present invention. The PEMF transducer system that the present invention uses may be formed and anatomically contoured for the shoulder, the wrist, the hip or other areas of the skeletal system. FIG. 1, in particular, shows a contoured triangular PEMF transducer 10 that is anatomically contoured for providing PEMF stimulation therapy to the shoulder area. That is, one side is curved to fit over the top of the shoulder so that corresponding angular areas are positioned in front and in back of the shoulder, with the other sides being curved down along the upper arm. The shoulder transducer is an integral unit including drive electronics and control electronic that may be held in place by a body strap.

FIG. 2 shows placement of a PEMF stimulation therapy device that includes a PEMF stimulation transducer 12 according to the teachings of the present invention, but of a size and shape that best suits the patient's wrists or other limb portion. PEMF transducer drive circuitry and control electronics preferably are made as an integral part of PEMF stimulation transducer 12.

FIG. 3 shows yet another embodiment of the present invention as hip belt PEMF stimulation therapy device 18 that a patient may wear around the waist, the PEMF transducer 20 arranged over the hip area. The drive electronics and control circuitry, again, is an integral part of PEMF stimulation therapy device 18.

Figure 4:
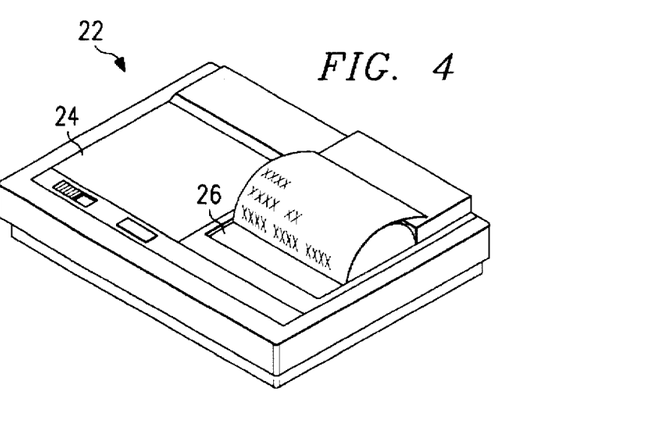
FIG. 4 a read-out unit that may be used for displaying and recording a user's operation of the present invention.

FIG. 4 shows a read-out unit 22 that may be used for displaying and recording a patient's operation of the present invention. The present invention may include, therefore, an extended memory and built-in printer interface 24 for providing the ability to correlate patient usage with desired healing progress and provide results on a paper printout device 26. The system of the present embodiment, for example, may store months of compliance data for developing important correlation data and print out such data using paper printout device 26.

2. PEMF Transducer Design and Fabrication

Figure 5:
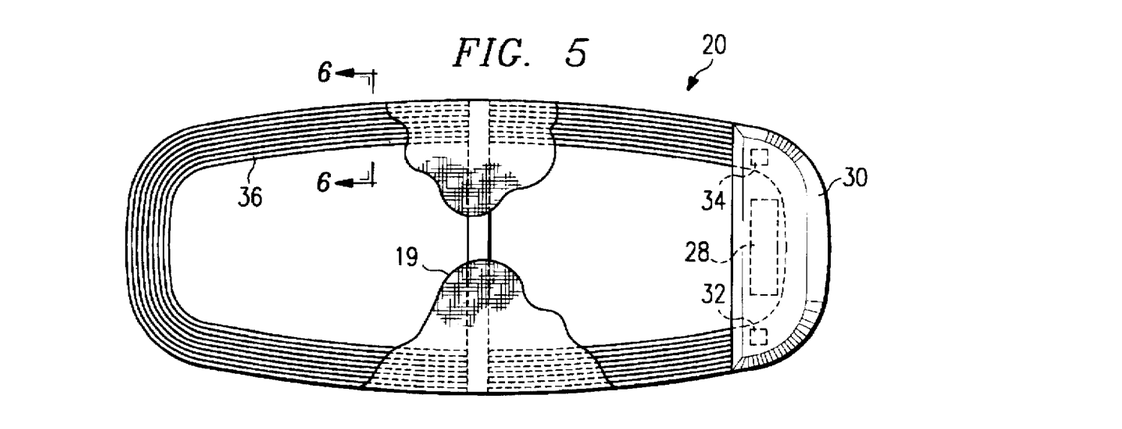
FIGS. 5 and 6 illustrate an exemplary PEMF stimulation therapy transducer and associated control and drive electronics formed according to the present invention.
Figure 6:
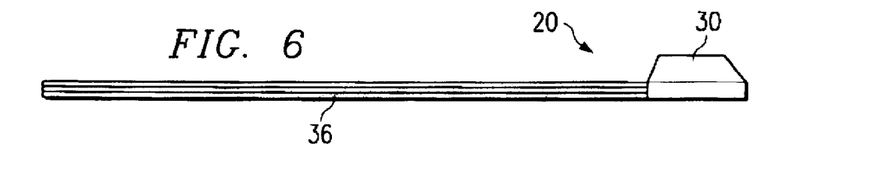

FIGS. 5 and 6 illustrate the construction of a PEMF transducer coil and associated electronics that may be, for example, that of PEMF device 18 of FIG. 3 As FIG. 6 shows, PEMF transducer 20 may have a substantially flat cross-sectional profile, which is a result of its flat-wound construction. PEMF transducer 20 is semi-rigid to maintain a desired contour and profile, but is bendable by the patient or health care professional to customize or alter according to the anatomical contour. PEMF transducer 20 includes flat-wound a PEMF winding that is encapsulated in a shell of a plasticized elastomer material (such as polyurethane) with a selected degree of rigidity.

PEMF transducer 20 includes PEMF windings that provide the PEMF stimulation signals and drive electronics that assist in tailoring the operation of PEMF transducer 20. Drive electronics 28 is encapsulated into a partial circuit board and encapsulated in a thermoplastic shell 30 that covers the end of PEMF transducer coil 36. The circuit board carrying drive electronics 28 is coupled to the PEMF winding of PEMF transducer coil 36, with the winding wires exiting the PEMF transducer coil 36 bundle in the areas 32 and 34.

The control electronics module 28 is integral to PEMF device 18, and includes a PEMF signal processor for providing pulsing current to PEMF transducer 20 at predetermined intervals, thereby activating the PEMF stimulation signal according to a prescribed pre-programmed PEMF regimen.

To implement a PEMF stimulation therapy program, a health care professional determines a regimen of PEMF stimulation of the affected body portion. The prescribed PEMF therapy regimen is translated into a PEMF program, which is programmed into a PEMF memory in control electronics module 28, either during manufacture or subsequently.

For patient use, PEMF transducer 20 may be placed into a Velfoam® pouch or other soft covering preferably using Velcro fasteners of PEMF stimulation therapy device 18, for example. As stated above, the semi-rigid PEMF transducer shell is sufficiently flexible to permit the patient or a health care professional to adjust the anatomical contour. This arrangement relies on a soft but semi-rigid support of the PEMF stimulation therapy device 18, with PEMF transducer 20 being contoured around the affected body part. Once the PEMF stimulation therapy device 18 is in place, the patient starts the PEMF program by turning on control electronics module 28.

In accordance with the stored PEMF therapy program, the PEMF processor correspondingly controls the activation current supplied to PEMF transducer 20, thereby controlling the PEMF stimulation signals in terms of energization time, de-energization time, and duty cycle or repetition rate. In addition to controlling the PEMF therapy, the PEMF processor maintains treatment data that is available on request to the patient (through a small display), and to a health care professional (via an I/O port) for monitoring and analysis.

Figure 7:
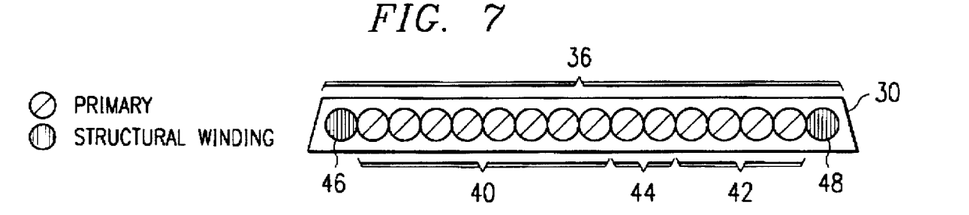
FIG. 7 is an exemplary winding pattern for the PEMF transducer coil circuit of the present invention.

FIG. 7 is a cross-sectional view of PEMF transducer 28 that includes PEMF windings 40, 42 and 44 surrounded by optional structural windings 46 and 48 and encapsulated in a semi-rigid shell 30.

For an exemplary embodiment, PEMF transducer 20 includes two parallel PEMF windings of about 7 turns each. For the PEMF windings, 18 gauge wire can be used. The approximate dimensions of the winding bundle are 0.75 by 0.12 inches, while the approximate dimensions of the shell are 1.50 by 0.31 inches.

The winding material is a commercially available hook-up wire. Shell 30 may be a polyurethane-type elastomer material, also available commercially. Other materials for shell 30 can be used to provide different degrees of transducer-shell rigidity, thereby providing different bracing rigidity characteristics.

The PEMF windings are wound simultaneously in a winding machine around a flat mandrel of the appropriate triangular shape for the transducer. The PEMF windings are maintained in the flat-wound position shown in FIG. 7 by parallel side plates. Once wound, the start and finish wire ends for each winding are cut to provide leads for coupling to the drive electronics, and the winding assembly—winding bundle, mandrel and side plates—is removed from the winding machine. The mandrel includes slots. An adhesive, typically a UV-curable adhesive is placed on the coil through the slots in the mandrel. Then, the entire mandrel assembly is placed within a UV light chamber for curing the unit. The winding bundle is now in a flexible, bonded unit.

Next, the circuit board (not shown) with drive electronics 28 is positioned according to particular desired configuration of the PEMF transducer 20 and may be secured by a variety of mechanisms, such as by adhesive tape, a clamp, or a clam-shell housing made of plastic or another material. The winding leads of the transducer and the wires of a cable are attached to the drive electronics board, such as by soldering.

The winding bundle for PEMF transducer 20 is placed in a mold. Then, the polyurethane elastomer is molded with the coil in place. This permits separately molding a space in the polyurethane, thermoplastic elastomer, or PVC material so that the mold may be fitted over and encapsulate the winding. In one embodiment, a two-component polyurethane elastomer may be separately cast, or made of an injection moldable material such as PVC or Santoprene® (which is a thermoplastic elastomer). Thus, in contrast to molding PEMF transducer 20 in place, the mold is formed separately and PEMF transducer 20 is fit together with the mold.

Finally, after placing PEMF transducer 20 into the molded shell, a backing may be placed on PEMF transducer 20 that is also a flexible plastic, such as Kydex® or some other flexible plastic sheet, and PEMF transducer 20 is then glued or snapped into place. Then PEMF transducer 20 may be introduced into a bending fixture to be bent into the desired anatomical contour. Alternately, PEMF transducer 20 may be covered with a Velfoam® or neoprene sheath for wrapping about a wrist or ankle, such as in the embodiment of FIG. 2.

In still another embodiment, a Metglas® configuration may be used for core coils that form PEMF transducer 20. The Metglas® configuration uses a core holder, which is an essentially flat plastic case that is similar to that in which a videocassette may be packaged, but is somewhat thinner. The material known as Metglas®, which is a flexible ferrite material, which has high permeability, has the ability to store electromagnetic energy. This allows Metglas® to serve as a core material for PEMF transducer 20. The Metglas® material may be formed as a core for PEMF transducer 20 in the shape of a toroid or other appropriate transducer shape.

The Metglas® material may be placed in a polyethylene core holder that may then be snapped shut. Then the assembled structure may be placed into a winding machine, which operates as does a lathe with a chuck on each end. This is spun to wind the single winding along the length of the core holder. The core holder is essentially rectangular at this point. The core holder is then removed from the winding machine and bent under heat to form a "U" or horseshoe shape. Then, the core holder is covered with a Velfoam® or other material such as neoprene, to form a sheath over the core holder. Then, a plastic clamp holder may be placed containing the control and drive electronics circuitry on either end. Other embodiments that achieve the purposes of the present invention may also be used.

3. Control and Drive Electronics

Figure 8:
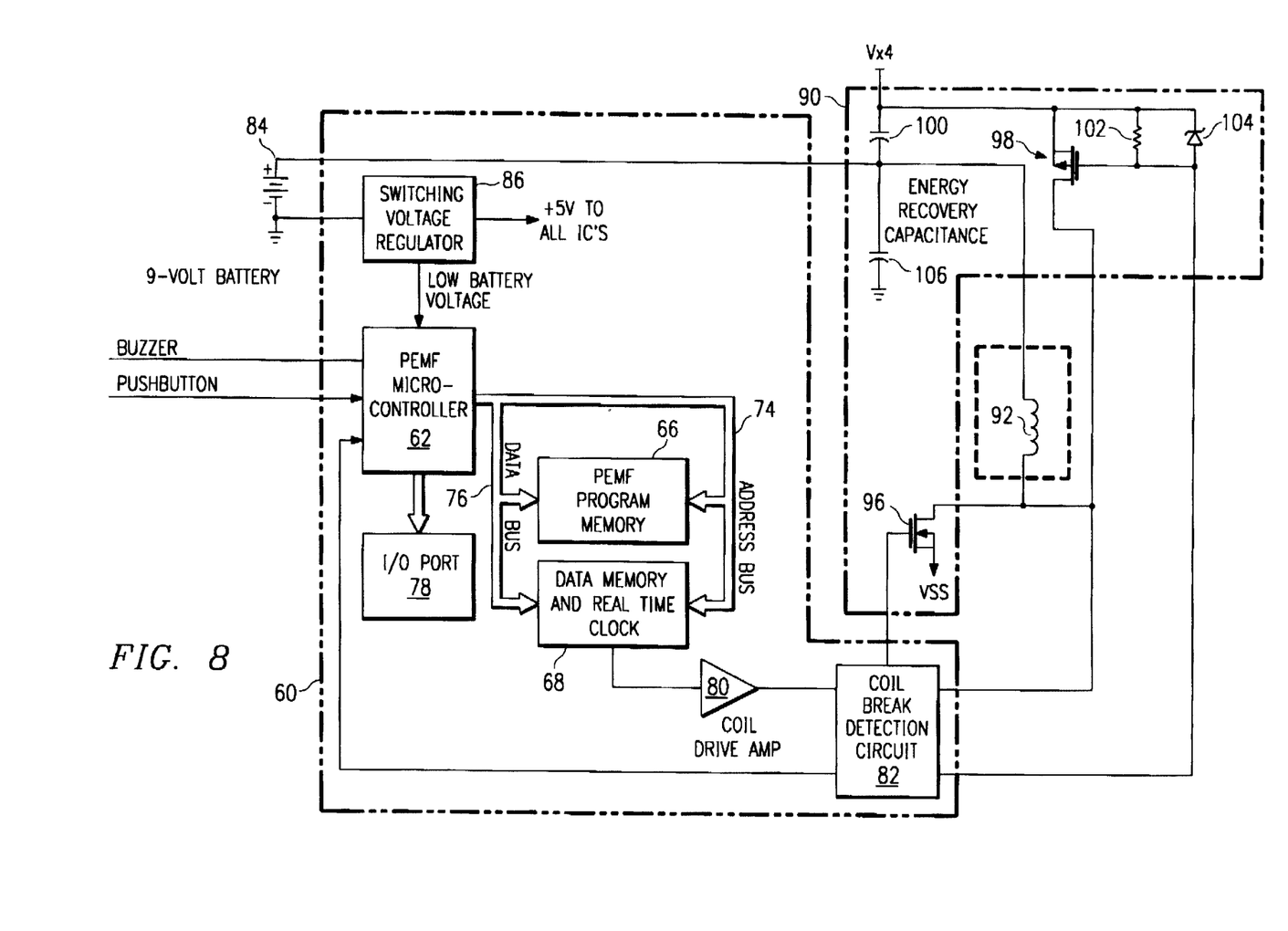
FIG. 8 is a schematic block diagram of the control electronics and the drive electronics for the PEMF transducer system of the present invention.

FIG. 8 is a schematic block diagram of the control electronics and the drive electronics of the present invention, which are physically located respectively in the control electronics module 28 and encapsulated within the shell 30 of the PEMF transducer 20. Control electronics 60 includes a PEMF processor 62, with associated integrated circuit components: a PEMF internal program memory 66, a data memory and real time clock circuit 68. PEMF processor 62 is coupled to these components by address bus 74 and data bus 76. A PEMF program can be loaded into a microcontroller EPROM or other memory and installed as PEMF program memory 66. Alternatively, the PEMF program can be read into the PEMF program memory via an I/O port 78. Data collected during execution of the programmable PEMF program parameters—such as start time, stop time, duration, and daily average—is stored in the data memory 68, and can be read out to a printer (or over a communications link) via the I/O port 78.

The PEMF processor 62 controls transducer drive amplifier 80. The coil drive amplifier controls the energization and de-energization of PEMF transducer 20. Coil break detection circuit 82 senses the resulting electromagnetic fields and provides an appropriate signal to PEMF processor 62. PEMF processor 62 receives power from a power source, such as a nine-volt lithium or alkaline battery 84, for example, through a switching voltage regulator 86 (which also provides +5 volts power to the other integrated circuit components).

PEMF processor 62 and the supporting integrated circuit CMOS logic chips function conventionally and are commercially available. For the exemplary embodiment, PEMF processor 62 may be an Motorola 68HC11 processor. The data memory and real time clock integrated circuit 68 is a Dallas Semiconductor Corporation device, used to store representative data about the patient's use of the PEMF system based on the internally maintained clock and calendar.

For the exemplary embodiment, the PEMF program outputs two programmed pulse trains. Each of the two pulse trains provides 99 pulses that in one embodiment collectively last 25,740 microseconds. Each of the pulse trains is offset, such that when one pulse is high the other pulse is low. This alternating flow permits driving the drive electronics so that it switches the current on and off at the proper times to provide the desired recovery phase of operation. In one example, therefore, the first signal may be ON for 67 microseconds and OFF for 195 microseconds. Accordingly, the second pulse train will include a 195 ON period followed by a 67 second OFF period. The two pulse trains may be provided every 667,000 microseconds.

One important aspect of the present invention is that at the beginning of the two pulse trains, the first pulse is a shorter pulse than the other pulses in the same pulse train. Thus, if the first pulse train includes 65 microsecond on and 195 microsecond off times, then the first pulse of the first pulse train may be preferably 32.5 microseconds. This first short pulse sets up the magnetic field for the PEMF stimulation therapy signal in the single-winding coil. By turning on the drive circuitry for one-half pulse, energization of the magnetic field takes place to set the PEMF magnetic field away from zero. With this setting, the next pulse on the lower train turns on for 195 seconds. This sets the current so that the drive flyback energy goes in a negative direction. This causes the remaining cycling to flow from an initial negative direction. The current then ramps up through zero and increases from a negative number through zero to a positive number during the pulse. Thus, because the current is changing in the inductor that the PEMF transducer forms, a constant electrical field is induced. The first half pulse establishes the constant PEMF field for delivering the desired PEMF therapy signal.

Drive electronics 90 controls activation of PEMF transducer coil 36 and the generation of the PEMF stimulation therapy signals. FIG. 8 represents PEMF transducer coil 36 by PEMF winding 92. Drive electronics 90 includes FET switch 96 that connects between coil break detection circuit 82 and PEMF winding 92 and FET switch 98 that connects between capacitor 100 and PEMF winding 92. Capacitor 100, resistor 102 and parallel zener diode 104, control operation of FET switch 98. FET switches 96 and 98 control the PEMF stimulation signal that is output from PEMF winding 92.

In initialization, FET switch 96 is turned on by coil drive amp 80 to present battery voltage across PEMF winding 92 for a period of one-half a normal pulse duration of typically 65 microseconds. Activation current from battery 84, therefore, flows through PEMF winding 92 to generate the PEMF transducer 20 output signals. When FET switch 96 switches off, FET switch 98 switches on to charge capacitor 100 to a voltage equal to four times the battery voltage. This causes the transducer to discharge in the opposite direction during the off period for FET switch 96. Thus, energy recovery occurs without a secondary coil, unlike the case with known systems, and is more efficient. This is because there are no coupling losses that exist with the secondary winding. Since the recovery voltage is four times the available battery voltage, drive circuit 90 permits sequencing of the current through PEMF winding 92 to flow in both directions. Therefore, for a given magnetic field strength, the peak current can be cut in half. This results in a factor of four reduction in $I^2R$ losses, where I is the instantaneous coil current and R is the resistance of the coil winding. These are the types of losses that would exist with the use of a secondary winding. With the preferred embodiment of the invention, the voltage $V_{X4}$ may be derived using the flyback pulse from PEMF winding 92, instead of requiring a separate voltage boost circuit. Thus, by virtue of balancing the capacity of capacitors 100 and 106, it is possible to eliminate the need for a separate four-times voltage supply circuit.

Coil break detection circuit 82 senses the electromagnetic fields generated during PEMF transducer activation and provides feedback to PEMF microcontroller 62 for monitoring the operation of PEMF stimulation device operation, for example. PEMF microcontroller 62 causes appropriate monitoring data to be stored in data memory and real time clock 68, and will initiate an alarm signal in the case of malfunction.

Figure 9:
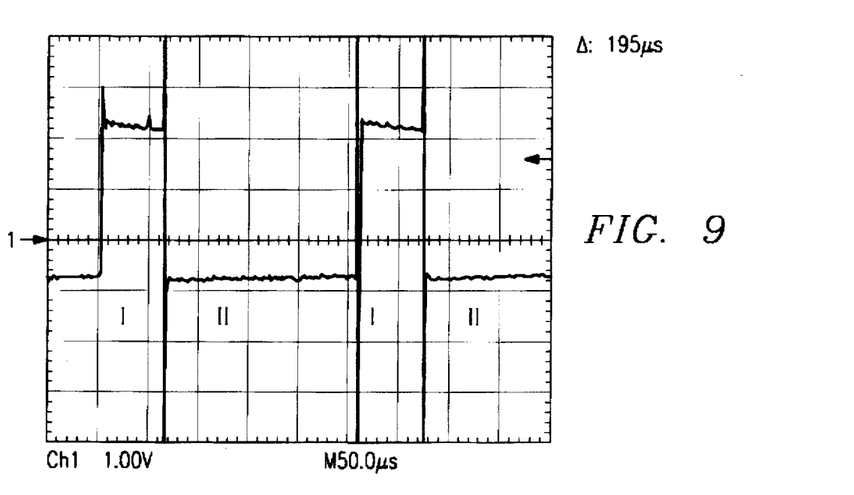
FIG. 9 shows an example of the waveform that the transducer coil of the present invention generates.

FIG. 9 shows an example of the waveform that the transducer coil of the present invention generates. Note that the high voltage is one-third the duration and three times the magnitude of the low voltage. FIG. 9 shows the PEMF stimulation signal output from PEMF winding 92 which includes a transformer pulse positive portion I followed by transformer pulse negative portion II. Pulse position portion I has a duration of approximately 65 microseconds. Pulse negative portion II has a duration of approximately 195 microseconds. The positive voltage level for transformer pulse positive portion I is approximately three times the negative voltage level for pulse negative portion II. The areas of the portions I and II, therefore, are approximately equivalent.

Figure 10:
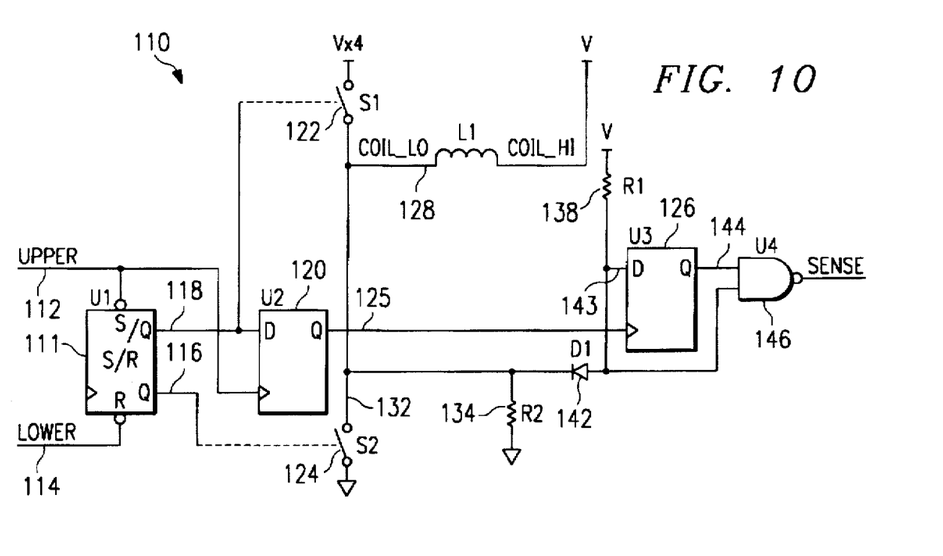
FIG. 10 shows a schematic diagram of the coil break detection circuit of the present invention.

FIG. 10 provides one embodiment of the system of FIG. 8 that uses digital circuitry of coil break detection circuit 82 that detects a field-fault condition in the PEMF stimulation therapy device of the present invention. The digital circuitry 110 includes U1 set/reset flip-flop 111 that receives upper input 112 and lower input 114 to output Q output 116 and /Q output 118. The /Q output 118 goes to U2 flip-flop 120 and controls the operation of S1 switch 122. The Q output 116 controls the operation of S2 switch 124. The Q output 125 from U2 flip-flop 120 goes to U3 flip-flop 126 as a clock signal. The S1 switch 122 controls whether the COIL_LO from L1 field winding 128 goes to $V_{x4}$, while 52 switch 124 shunts COIL_LO from L1 field winding 128 to ground. The COIL_HI line provides supply voltage V to L1 field winding 128.

Line 132 between S1 switch 122 and S2 switch 124 connects to R2 resistor 134 and D1 diode 142, which receives supply voltage, V, from R1 resistor 138. U3 flip-flop 126 receives as its D input 143 the output from R1 resister 138. The Q output 144 from U3 flip-flop 126 goes to U4 NAND gate 146 to generate a sense output.

Figure 11:
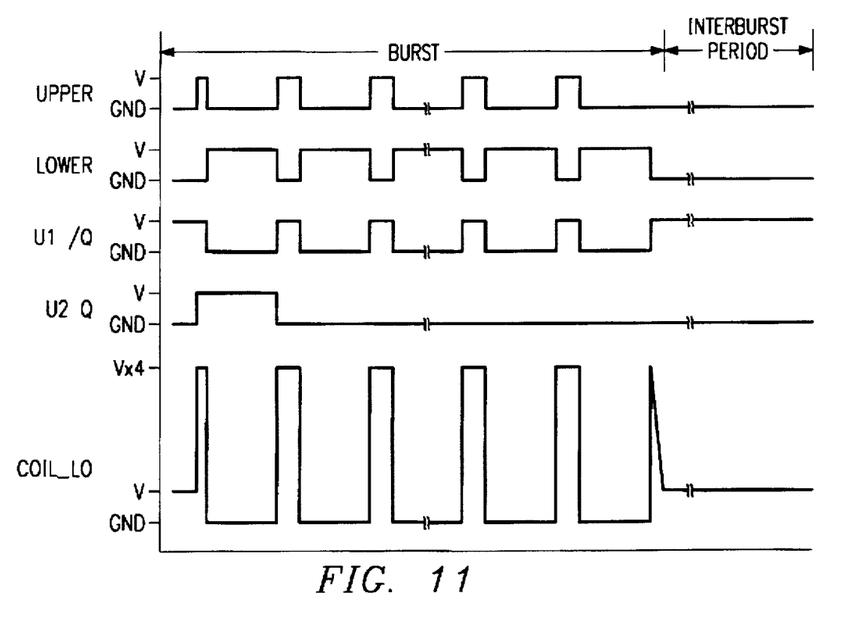
FIG. 11 shows a diagram of the input logic burst signal of the present invention.

In operation, digital circuitry 110 has drive circuit elements including U1 flip-flop 111, S1 switch 122, S2 switch 124, and L1 field winding 128. The voltage $V_{X4}$ is four times the voltage V; both being measured with respect to ground. The UPPER and LOWER signals consist of a burst of pulses, separated by an inter-burst period, as shown in FIG. 11. These two signals are essentially non-overlapping ensuring the stable operation of the U1 set-reset flip-flop, 111.

The Q and /Q outputs of U1 set/reset flip-flop 111 are of opposite state and are also essentially non-overlapping, ensuring S1 switch 122 and S2 switch 124 are never simultaneously conducting.

The coil break detection circuitry components of digital circuitry 110 include U2 flip-flop 120, U3 flip-flop 126, U4 NAND gate 146, D1 diode 142, R1 resistor 138, and R2 resistor 134. The COIL_LO signal, with L1 field winding 128 in place, is as shown in FIG. 11. During the burst, COIL_LO transitions between $V_{x4}$ and Ground.

During the inter-burst period, and S1 switch 122 and S2 switch 124 are open. Under normal operating conditions, L1 field winding 128 will pull the COIL_LO signal level to the supply voltage V. If a break should occur in the coil, the COIL_LO signal will be pulled to ground by R2 resistor 134.

R1 resistor 138, R2 resistor 134 and D1 diode 142 translate the COIL_LO signal to levels appropriate for the inputs of U3 flip-flop 126 and U4 NAND gate 146. The ratio of R1 resistor 138 to R2 resistor 134 is selected to provide a logic level "0" at the inputs of U3 flip-flop 126 and U4 NAND gate 146 should a break occur in L1 field winding 128.

The output of U2 flip-flop 120 is a single pulse occurring at the beginning of a burst, beginning with the first pulse of UPPER and terminating on the second pulse of UPPER. The rising edge of the output of U2 flip-flop 120 occurs prior to the first rising edge of COIL_LO due to the relatively short time delay associated with U2 flip-flop 120 versus S1 switch 122 and S2 switch 124. The sampling pulse output of U2 is fed to U3 which samples the inter-burst voltage. If the inter-burst voltage is equal to V, the Q output 144 of U3 flip-flop 126 will be set to a logic level "1" until the next sampling pulse, thereby enabling output of the inverse of the COIL_LO signal to the processor as the SENSE signal.

If the inter-burst voltage is at a ground level, due to a break in L1, the output of U3 will be set to a logic level "0", disabling the output of the inverse of the COIL_LO signal to the processor.

A short across the coil terminals will cause the COIL_LO signal to be tied to V. The output of U3 flip-flop 126 will be a logic level "1," therefore the output of U4 NAND gate 146 will be a logical level "0" rather than the burst signal that PEMF microcontroller 62 normally expects. This indicates the existence of a field fault condition to the PEMF microcontroller 62.

Connecting either the COIL_HI or COIL_LO terminal to ground, will essentially create a DC short of the power to the unit and a loss of power.

FIG. 11 shows a diagram of the logic burst signal of the present invention, that in greater detail depicts the duration relationship between the upper and lower logic signals. In each logic burst signal, there are a number of pulses, the duration of each upper pulse being only one-third the duration of lower pulse. Other parameters may also be used.

Figure 12:
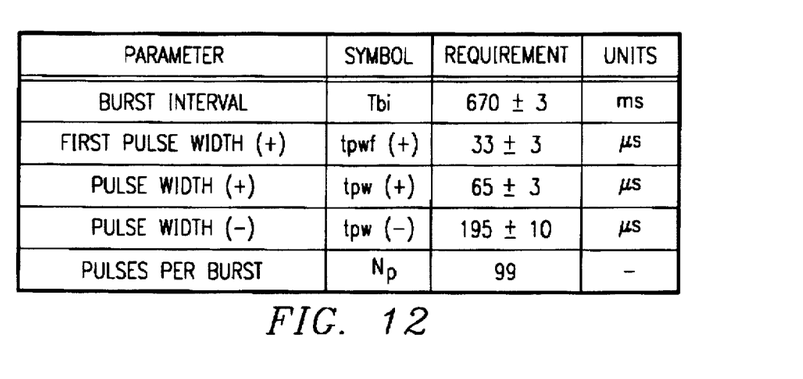
FIG. 12 provides a table of typical parameters, requirements, units, and symbols that correspond to the diagrams of FIGS. 9 and 11.

FIG. 12 provides a table of parameters, requirements, units, and symbols that correspond to the diagrams of FIG. 11. In the table of FIG. 12, the example includes a burst interval of 670 milliseconds, during which a first pulse width is 33 microseconds. Thereafter the upper pulse width is 65 microseconds. The lower pulse width is 195 microseconds. For the example of FIG. 12, which can easily produce the input that FIG. 11 depicts, there are 99 pulses per burst. The present invention may also use other timing parameters to achieve the desired PEMF signals and associated energy recovery operation.

4. Conclusion

Although the invention has been described with respect to a specific, exemplary embodiment, various changes and modifications may be suggested to one skilled in the art. For example, the control and drive electronics may be different from those of the above-described embodiments. In such an alternative embodiment, for example, the control and drive electronics may be detached from the PEMF transducer 20 with an electrical cord existing there between. Therefore, it is intended that the invention encompass all changes and modifications that fall within the scope of the appended claims.

What is claimed is:

1. A PEMF transducer for a bone growth stimulator device, consisting essentially of:
   a single-winding transducer coil for receiving a supply voltage from a voltage supply and in response thereto generating a PEMF stimulation therapy signal; and
   a drive circuit for recovering flyback energy from the single-winding transducer coil and dumping a voltage equal to a predetermined voltage differing from said supply voltage for sequencing the current through the transducer coil in a positive direction and negative direction.

2. The PEMF transducer of claim 1, further comprising coil break detection circuitry for sensing the proper operation of said PEMF transducer.

3. The PEMF transducer of claim 2, wherein said coil break detection circuitry comprises circuitry for determining a short across said single-winding transducer coil.

4. The PEMF transducer of claim 1, wherein said predetermined voltage has a value of at least approximately four times said supply voltage.

5. The PEMF transducer of claim 1, wherein said drive circuitry generates an upper signal and a lower signal, each comprising a burst of pulses, for generating said PEMF stimulation therapy signal, said upper signal and lower signal having opposite states and non-overlapping values.

6. A method for generating a PEMF stimulation therapy signal for bone growth stimulation, consisting essentially of the steps of:
   receiving a supply voltage from a voltage supply and in response thereto generating a PEMF stimulation signal from a single-winding transducer coil; and
   recovering flyback energy with a drive circuit from said single-winding transducer coil and said drive circuit dumping the flyback energy to a voltage equal to a predetermined voltage differing from said supply voltage for sequencing the current through the transducer coil in a positive direction and negative direction, thereby generating the PEMF stimulation signal.

7. The PEMF signal output generating method of claim 6, further comprising the step of determining a short across the single-winding transducer coil using coil break detection circuitry.

8. The PEMF signal output generating method of claim 6, further comprising the step of dumping said flyback energy to a predetermined voltage having a value of at least approximately four times said supply voltage.

9. The PEMF signal output generating method of claim 6, further comprising the step of generating from said drive circuitry an upper signal and a lower signal having opposite states and non-overlapping values for generating said PEMF stimulation therapy signal.

10. A coil break detection circuit for determining and reporting a break in a PEMF transducer coil, consisting essentially of:
   a first switch circuit for switchably connecting said PEMF transducer coil to a predetermined voltage related to a supply voltage;
   a second switch circuit for switchably connecting said PEMF transducer coil to a ground potential;

a coil break detection sense circuit associated with said first switch circuit and said second switch circuit for generating a first output signal corresponding to proper PEMF transducer coil operation from receiving said supply voltage and a second output signal corresponding to a coil break condition in response to receiving said ground potential; and output circuitry for providing said first and second output signals to a processor associated with said PEMF transducer coil.

11. The coil break detection circuit of claim 10, wherein said coil break detection sense circuit further comprises a digital flip-flop circuit for generating a logic "1" in response to receiving said supply voltage and a logic "0" in response to receiving said ground potential.

12. The coil break detection circuit of claim 10, wherein said first switch and said second switch connect to a low side output of said PEMF transducer coil.

13. The coil break detection circuit of claim 10, wherein said coil break detection sense circuit receives either said supply voltage or said ground potential through said first or second switch circuits during the period between signal bursts generated from said PEMF transducer coil.

\* \* \* \* \*